(12) United States Patent
Conway et al.

(10) Patent No.: US 9,872,969 B2
(45) Date of Patent: Jan. 23, 2018

(54) CATHETER IN BAG WITHOUT ADDITIONAL PACKAGING

(71) Applicant: Rochester Medical, Stewartville, MN (US)

(72) Inventors: Anthony J. Conway, Chatfield, MN (US); Sarah L. Grinde, Spring Grove, MN (US)

(73) Assignee: Rochester Medical Corporation, a subsidiary of C.R. Bard, Inc., Stewartville, MN (US)

( * ) Notice: Subject to any disclaimer, the term of this patent is extended or adjusted under 35 U.S.C. 154(b) by 844 days.

(21) Appl. No.: 13/682,420

(22) Filed: Nov. 20, 2012

(65) Prior Publication Data

US 2014/0142555 A1    May 22, 2014

(51) Int. Cl.
*A61M 25/00*    (2006.01)
*A61B 50/36*    (2016.01)

(52) U.S. Cl.
CPC .......... *A61M 25/002* (2013.01); *A61B 50/36* (2016.02); *A61M 25/0017* (2013.01)

(58) Field of Classification Search
CPC ............ A61M 25/0017; A61M 25/002; A61M 2202/0496; A61M 2210/1085; A61M 2210/1089; A61M 25/0111; A61M 2210/1078; A61M 25/01; A61M 25/0113; Y10S 128/24; A61B 19/0256; A61B 19/026; A61B 19/0264; A61B 19/0271; A61F 13/55115; A61F 13/55105; A61F 13/551; A61F 13/5513; A61F 13/55135; A61F 13/55145; A61F 13/5516; A61F 13/55165; A61F 13/55175; A61F 13/55185; A61F 13/5519; A61F 15/001; A61F 15/00; A61F 13/00072; A61F 13/00076
USPC ....... 604/544, 540, 328, 257, 262, 265, 523, 604/93.01, 163; 53/461, 163, 466, 116, 53/562, 586, 228, 371.7, 372.2, 372.5, 53/372.7, 3, 74.7, 375.2, 375.5, 375.7
See application file for complete search history.

(56) References Cited

U.S. PATENT DOCUMENTS

| | | | |
|---|---|---|---|
| 480,911 | A | 8/1892 | Vance |
| 822,092 | A | 5/1906 | Woodruff |
| 1,235,142 | A | 7/1917 | Ichilian |
| 1,643,289 | A | 9/1927 | Peglay |
| 1,661,494 | A | 3/1928 | Nielsen |
| 2,043,630 | A | 6/1936 | Raiche |
| 2,213,210 | A | 9/1940 | Egbert |
| 2,228,992 | A | 1/1941 | Fry |

(Continued)

FOREIGN PATENT DOCUMENTS

| | | |
|---|---|---|
| CA | 763930 A | 7/1967 |
| CN | 101896218 A | 11/2010 |

(Continued)

OTHER PUBLICATIONS

Amirkhalili, Saeid et al., "Mitric Oxide Complexes of Trimethylaluminium," Jornal of Organometallic Chemistry, 149 (Jan. 20, 1978) 407-411.

(Continued)

*Primary Examiner* — Adam Marcetich
(74) *Attorney, Agent, or Firm* — Rutan & Tucker, LLP

(57) ABSTRACT

The present invention relates to a urinary catheter and collection bag that can be provided without additional packaging.

35 Claims, 4 Drawing Sheets

(56) References Cited

U.S. PATENT DOCUMENTS

| | | |
|---|---|---|
| 2,230,226 A | 2/1941 | Auzin |
| 2,248,934 A | 7/1941 | Auzin |
| 2,285,502 A | 6/1942 | Dreyfus |
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 3,044,468 A | 7/1962 | Birtwell |
| 3,053,257 A | 9/1962 | Birtwell |
| 3,076,464 A | 2/1963 | Rosenberg |
| 3,154,080 A | 10/1964 | Rowan et al. |
| 3,169,527 A | 2/1965 | Sheridan |
| 3,211,151 A | 10/1965 | Foderick et al. |
| 3,304,353 A | 2/1967 | Harautuneian |
| 3,345,988 A | 10/1967 | Vitello |
| 3,394,704 A | 7/1968 | Dery |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,503,400 A | 3/1970 | Osthagen |
| 3,508,959 A | 4/1970 | Krahnke |
| 3,509,884 A | 5/1970 | Bell |
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,683,928 A | 8/1972 | Kuntz |
| 3,695,921 A | 10/1972 | Shepard et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,838,728 A | 10/1974 | Voegele |
| 3,841,304 A | 10/1974 | Jones |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,903,893 A | 9/1975 | Scheer |
| 3,924,634 A | 12/1975 | Taylor et al. |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,055,682 A | 10/1977 | Merrill |
| 4,062,363 A | 12/1977 | Bonner, Jr. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch |
| 4,266,999 A | 5/1981 | Baier |
| 4,269,310 A | 5/1981 | Uson |
| 4,284,459 A | 8/1981 | Patel et al. |
| 4,287,227 A | 9/1981 | Kamada et al. |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,342,392 A * | 8/1982 | Cox .................. 206/438 |
| 4,343,788 A | 8/1982 | Mustacich et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,446,860 A | 5/1984 | Gutnick |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,515,593 A | 5/1985 | Norton |
| 4,534,768 A | 8/1985 | Osburn et al. |
| 4,539,234 A | 9/1985 | Sakamoto et al. |
| 4,540,409 A | 9/1985 | Nystrom et al. |
| 4,553,533 A | 11/1985 | Leighton |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,612,337 A | 9/1986 | Fox, Jr. et al. |
| 4,613,324 A | 9/1986 | Ghajar |

(56) References Cited

U.S. PATENT DOCUMENTS

| | | |
|---|---|---|
| 4,615,692 A | 10/1986 | Giacalone et al. |
| 4,615,697 A | 10/1986 | Robinson |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,633,863 A | 1/1987 | Filips et al. |
| 4,634,433 A | 1/1987 | Osborne |
| 4,637,907 A | 1/1987 | Hegel et al. |
| 4,638,790 A | 1/1987 | Conway et al. |
| 4,640,668 A | 2/1987 | Yang |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,699,616 A | 10/1987 | Nowak et al. |
| 4,710,169 A | 12/1987 | Christopher |
| 4,710,181 A | 12/1987 | Fuqua |
| 4,731,064 A | 3/1988 | Heyden |
| 4,737,219 A | 4/1988 | Taller et al. |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,768,503 A | 9/1988 | Highgate et al. |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| 4,919,966 A | 4/1990 | Shlenker |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,952,618 A | 8/1990 | Olsen |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,059,190 A | 10/1991 | Novak |
| 5,071,406 A | 12/1991 | Jang |
| 5,078,707 A | 1/1992 | Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,176,666 A | 1/1993 | Conway et al. |
| 5,197,957 A | 3/1993 | Wendler |
| 5,201,724 A | 4/1993 | Hukins et al. |
| 5,209,726 A | 5/1993 | Goosen |
| 5,211,640 A | 5/1993 | Wendler |
| 5,226,530 A | 7/1993 | Golden |
| 5,234,411 A | 8/1993 | Vaillancourt |
| 5,236,422 A | 8/1993 | Eplett, Jr. |
| 5,242,391 A | 9/1993 | Place et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,279,600 A | 1/1994 | Hogan |
| 5,290,306 A | 3/1994 | Trotta et al. |
| 5,300,052 A | 4/1994 | Kubo |
| 5,306,226 A | 4/1994 | Salama |
| 5,334,175 A | 8/1994 | Conway et al. |
| 5,335,775 A * | 8/1994 | Scanlon et al. .............. 206/63.3 |
| 5,336,211 A | 8/1994 | Metz |
| 5,346,483 A | 9/1994 | Thaxton, Sr. |
| 5,348,536 A | 9/1994 | Young et al. |
| 5,352,182 A | 10/1994 | Kalb et al. |
| 5,360,402 A | 11/1994 | Conway et al. |
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,402,886 A | 4/1995 | McGlinch |
| 5,409,495 A | 4/1995 | Osborn |
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,447,231 A | 9/1995 | Kastenhofer |
| 5,451,424 A | 9/1995 | Solomon et al. |
| 5,454,798 A | 10/1995 | Kubalak et al. |
| 5,464,650 A | 11/1995 | Berg et al. |

(56) References Cited

U.S. PATENT DOCUMENTS

| | | |
|---|---|---|
| 5,479,945 A | 1/1996 | Simon |
| 5,482,740 A | 1/1996 | Conway et al. |
| 5,483,976 A | 1/1996 | McLaughlin et al. |
| 5,501,669 A | 3/1996 | Conway et al. |
| 5,509,427 A | 4/1996 | Simon et al. |
| 5,513,659 A | 5/1996 | Buuck et al. |
| 5,513,660 A | 5/1996 | Simon et al. |
| 5,531,715 A | 7/1996 | Engelson et al. |
| 5,531,717 A | 7/1996 | Roberto et al. |
| 5,538,584 A | 7/1996 | Metz |
| 5,549,924 A | 8/1996 | Shlenker et al. |
| 5,554,141 A | 9/1996 | Wendler |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,593,718 A | 1/1997 | Conway et al. |
| 5,599,321 A | 2/1997 | Conway et al. |
| 5,614,143 A | 3/1997 | Hager |
| 5,622,711 A | 4/1997 | Chen |
| 5,624,395 A | 4/1997 | Mikhail et al. |
| 5,630,429 A | 5/1997 | Dann |
| 5,633,010 A | 5/1997 | Chen |
| 5,643,235 A | 7/1997 | Figuerido |
| 5,670,111 A | 9/1997 | Conway et al. |
| 5,670,557 A | 9/1997 | Dietz et al. |
| 5,671,755 A | 9/1997 | Simon et al. |
| 5,674,561 A | 10/1997 | Dietz et al. |
| 5,679,399 A | 10/1997 | Shlenker et al. |
| 5,695,485 A | 12/1997 | Duperret et al. |
| 5,702,381 A | 12/1997 | Cottenden |
| 5,707,357 A | 1/1998 | Mikhail et al. |
| 5,709,672 A | 1/1998 | Illner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,752,525 A | 5/1998 | Simon et al. |
| 5,756,144 A | 5/1998 | Wolff et al. |
| 5,762,996 A | 6/1998 | Lucas et al. |
| 5,779,632 A | 7/1998 | Dietz et al. |
| 5,779,670 A | 7/1998 | Bidwell et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,806,527 A | 9/1998 | Borodulin et al. |
| 5,810,789 A | 9/1998 | Powers et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,853,518 A | 12/1998 | Utas |
| 5,853,750 A | 12/1998 | Dietz et al. |
| 5,877,243 A | 3/1999 | Sarangapani |
| 5,895,374 A | 4/1999 | Rodsten et al. |
| 5,897,535 A | 4/1999 | Feliziani et al. |
| 5,902,631 A | 5/1999 | Wang et al. |
| 5,906,575 A | 5/1999 | Conway et al. |
| 5,931,303 A * | 8/1999 | Salvadori ............. 206/570 |
| 5,931,304 A * | 8/1999 | Hammond ............. 206/570 |
| 5,971,954 A | 10/1999 | Conway et al. |
| 5,980,483 A | 11/1999 | Dimitri |
| 5,980,507 A | 11/1999 | Fassuliotis et al. |
| 6,004,305 A | 12/1999 | Hursman et al. |
| 6,007,524 A | 12/1999 | Schneider |
| 6,007,526 A | 12/1999 | Passalaqua et al. |
| 6,050,934 A | 4/2000 | Mikhail et al. |
| 6,053,905 A | 4/2000 | Daignault, Jr. et al. |
| 6,059,107 A | 5/2000 | Nosted et al. |
| 6,063,063 A | 5/2000 | Harboe et al. |
| 6,065,597 A | 5/2000 | Pettersson et al. |
| 6,090,075 A | 7/2000 | House |
| 6,098,625 A | 8/2000 | Winkler |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,186,990 B1 | 2/2001 | Chen et al. |
| 6,206,885 B1 | 3/2001 | Ghahremani et al. |
| 6,231,501 B1 | 5/2001 | Ditter |
| 6,254,570 B1 | 7/2001 | Rutner et al. |
| 6,261,255 B1 | 7/2001 | Mullis et al. |
| 6,261,271 B1 | 7/2001 | Solomon et al. |
| 6,280,425 B1 | 8/2001 | Del Guercio |
| 6,296,627 B1 | 10/2001 | Edwards |
| 6,299,598 B1 | 10/2001 | Bander |
| 6,315,711 B1 | 11/2001 | Conway et al. |
| 6,326,421 B1 | 12/2001 | Lipman |
| 6,355,004 B1 | 3/2002 | Pedersen et al. |
| 6,379,334 B1 | 4/2002 | Frassica |
| 6,383,434 B2 | 5/2002 | Conway et al. |
| 6,387,080 B1 | 5/2002 | R.o slashed.dsten |
| 6,391,010 B1 | 5/2002 | Wilcox |
| 6,402,726 B1 | 6/2002 | Genese |
| 6,409,717 B1 | 6/2002 | Israelsson et al. |
| 6,437,038 B1 | 8/2002 | Chen |
| 6,440,060 B1 | 8/2002 | Latour, Jr. |
| 6,468,245 B2 | 10/2002 | Alexandersen |
| 6,479,000 B2 | 11/2002 | Conway et al. |
| 6,479,726 B1 | 11/2002 | Cole |
| 6,509,319 B1 | 1/2003 | Raad et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,626,888 B1 | 9/2003 | Conway et al. |
| 6,632,204 B2 | 10/2003 | Guldfeldt et al. |
| 6,634,498 B2 | 10/2003 | Kayerod et al. |
| 6,638,269 B2 | 10/2003 | Wilcox |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,716,895 B1 | 4/2004 | Terry |
| 6,719,709 B2 | 4/2004 | Whalen et al. |
| 6,723,350 B2 | 4/2004 | Burrell et al. |
| 6,733,474 B2 | 5/2004 | Kusleika |
| 6,736,805 B2 | 5/2004 | Israelsson et al. |
| 6,740,273 B2 | 5/2004 | Lee |
| 6,767,551 B2 | 7/2004 | McGhee et al. |
| D496,266 S | 9/2004 | Nestenborg |
| 6,787,156 B1 | 9/2004 | Bar-Shalom |
| 6,797,743 B2 | 9/2004 | McDonald et al. |
| 6,803,420 B2 | 10/2004 | Cleary et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,872,195 B2 | 3/2005 | Modak et al. |
| 6,887,230 B2 | 5/2005 | Kubalak et al. |
| 6,939,339 B1 | 9/2005 | Axexandersen et al. |
| 6,939,554 B2 | 9/2005 | McDonald et al. |
| 6,949,090 B1 | 9/2005 | Leers et al. |
| 6,951,902 B2 | 10/2005 | McDonald et al. |
| 7,001,370 B2 | 2/2006 | Kubalak et al. |
| 7,033,367 B2 | 4/2006 | Ghahremani et al. |
| 7,066,912 B2 | 6/2006 | Nestenborg et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,204,940 B2 | 4/2007 | McDonald et al. |
| 7,211,275 B2 | 5/2007 | Ying et al |
| 7,294,117 B2 | 11/2007 | Provost-tine et al. |
| 7,311,698 B2 | 12/2007 | Tanghoj et al. |
| 7,329,412 B2 | 2/2008 | Modak et al. |
| 7,331,948 B2 | 2/2008 | Skarda |

(56) References Cited

U.S. PATENT DOCUMENTS

| | | | |
|---|---|---|---|
| 7,334,679 B2 | 2/2008 | Givens, Jr. |
| 7,374,040 B2 | 5/2008 | Lee et al. |
| 7,380,658 B2 | 6/2008 | Murray et al. |
| 7,381,768 B2 | 6/2008 | Wiercinski et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,691,476 B2 | 4/2010 | Finley |
| 7,717,902 B2 | 5/2010 | Sauer |
| 7,749,529 B2 | 7/2010 | Ash et al. |
| 7,767,291 B2 | 8/2010 | Taylor |
| 7,770,726 B2 | 8/2010 | Murray et al. |
| 7,770,728 B2 | 8/2010 | Kærn |
| 7,780,642 B2 | 8/2010 | Rasmussen et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,052,673 B2 | 11/2011 | Nestenborg |
| 8,058,341 B2 | 11/2011 | Tosaki et al. |
| 8,066,693 B2 | 11/2011 | Tanghoj et al. |
| 8,127,922 B2 | 3/2012 | Nordholm et al. |
| 8,163,327 B2 | 4/2012 | Finley |
| 8,177,774 B2 | 5/2012 | House |
| 8,181,778 B1 | 5/2012 | Van Groningen et al. |
| 8,192,413 B2 | 6/2012 | Bjerregaard |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,298,202 B2 | 10/2012 | McCray |
| 8,303,556 B2 | 11/2012 | White |
| 8,328,792 B2 | 12/2012 | Nishtala et al. |
| 8,356,457 B2 | 1/2013 | Murray et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,864,730 B2 | 10/2014 | Conway et al. |
| 9,707,375 B2 | 7/2017 | Conway et al. |
| 2001/0001443 A1 | 5/2001 | Kayerod et al. |
| 2001/0031933 A1 | 10/2001 | Cannon |
| 2001/0054562 A1 | 12/2001 | Pettersson et al. |
| 2002/0013564 A1* | 1/2002 | Kubalek et al. ......... 604/385.01 |
| 2002/0032406 A1 | 3/2002 | Kusleika |
| 2002/0103467 A1 | 8/2002 | Kubalak |
| 2002/0147265 A1 | 10/2002 | Ding et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018321 A1 | 1/2003 | Rosenblum |
| 2003/0018322 A1 | 1/2003 | Tanghoj et al. |
| 2003/0055403 A1 | 3/2003 | Nestenborg et al. |
| 2003/0060807 A1 | 3/2003 | Tanghoj et al. |
| 2003/0083644 A1 | 5/2003 | Avaltroni |
| 2003/0114823 A1* | 6/2003 | Bosselaar et al. ........ 604/385.06 |
| 2003/0130646 A1 | 7/2003 | Kubalak et al. |
| 2003/0168365 A1 | 9/2003 | Kaern |
| 2004/0030301 A1 | 2/2004 | Hunter |
| 2004/0055925 A1* | 3/2004 | Franks-Farah et al. ...... 206/570 |
| 2004/0074794 A1 | 4/2004 | Conway et al. |
| 2004/0097892 A1 | 5/2004 | Evans et al. |
| 2004/0133156 A1 | 7/2004 | Diaz et al. |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0043715 A1 | 2/2005 | Nestenborg et al. |
| 2005/0049577 A1 | 3/2005 | Snell et al. |
| 2005/0070882 A1 | 3/2005 | McBride |
| 2005/0080399 A1 | 4/2005 | Bolmsjo et al. |
| 2005/0096688 A1 | 5/2005 | Slazas et al. |
| 2005/0101924 A1 | 5/2005 | Elson et al. |
| 2005/0109648 A1 | 5/2005 | Kerzman et al. |
| 2005/0137582 A1 | 6/2005 | Kull-Osterlin et al. |
| 2005/0148950 A1 | 7/2005 | Windheuser et al. |
| 2005/0177104 A1 | 8/2005 | Conway |
| 2005/0199521 A1 | 9/2005 | Givens |
| 2005/0214443 A1 | 9/2005 | Madsen |
| 2005/0282977 A1 | 12/2005 | Stempel et al. |
| 2005/0283136 A1 | 12/2005 | Skarda |
| 2006/0004332 A1 | 1/2006 | Marx |
| 2006/0025753 A1 | 2/2006 | Kubalak et al. |
| 2006/0041246 A1 | 2/2006 | Provost-tine et al. |
| 2006/0058777 A1 | 3/2006 | Nielsen |
| 2006/0163097 A1 | 7/2006 | Murray et al. |
| 2006/0196783 A1 | 9/2006 | Bruun et al. |
| 2006/0229576 A1 | 10/2006 | Conway et al. |
| 2006/0240069 A1 | 10/2006 | Utas et al. |
| 2007/0016168 A1 | 1/2007 | Conway |
| 2007/0088330 A1 | 4/2007 | House |
| 2007/0149946 A1 | 6/2007 | Viswanathan et al. |
| 2007/0161971 A1 | 7/2007 | House |
| 2008/0015527 A1 | 1/2008 | House |
| 2008/0091145 A1 | 4/2008 | House |
| 2008/0103464 A1 | 5/2008 | Mosler et al. |
| 2008/0172040 A1 | 7/2008 | Smith |
| 2008/0172042 A1 | 7/2008 | House |
| 2008/0179208 A1 | 7/2008 | Murray et al. |
| 2008/0183262 A1 | 7/2008 | Dowling |
| 2008/0215021 A1 | 9/2008 | Cisko, Jr. et al. |
| 2008/0243081 A1 | 10/2008 | Nance et al. |
| 2008/0279907 A1 | 11/2008 | Ash et al. |
| 2009/0000970 A1 | 1/2009 | Bordeau et al. |
| 2009/0005725 A1 | 1/2009 | Shorey |
| 2009/0043287 A1 | 2/2009 | Mosler et al. |
| 2009/0048570 A1 | 2/2009 | Jensen |
| 2009/0101531 A1 | 4/2009 | Nordholm et al. |
| 2009/0131917 A1 | 5/2009 | Kavanagh et al. |
| 2009/0163884 A1 | 6/2009 | Kull-Osterlin et al. |
| 2009/0200187 A1 | 8/2009 | Nestenborg et al. |
| 2009/0208368 A1 | 8/2009 | Waldrep et al. |
| 2009/0221992 A1 | 9/2009 | Hannon et al. |
| 2009/0234294 A1 | 9/2009 | Harvey et al. |
| 2009/0240214 A1* | 9/2009 | Conway et al. ............. 604/265 |
| 2010/0010086 A1 | 1/2010 | Ash et al. |
| 2010/0025273 A1* | 2/2010 | Matsuda et al. ............. 206/370 |
| 2010/0030197 A1 | 2/2010 | House |
| 2010/0036363 A1 | 2/2010 | Watanabe et al. |
| 2010/0133172 A1 | 6/2010 | Song et al. |
| 2010/0155268 A1 | 6/2010 | Murray et al. |
| 2010/0200002 A1* | 8/2010 | Orban Iii et al. ............. 128/853 |
| 2010/0240750 A1 | 9/2010 | Ash et al. |

(56) References Cited

U.S. PATENT DOCUMENTS

| | | | |
|---|---|---|---|
| 2010/0256576 A1 | 10/2010 | Aggarwal et al. | |
| 2010/0322996 A1 | 12/2010 | Wibaux et al. | |
| 2011/0056852 A1 | 3/2011 | Frojd | |
| 2011/0060317 A1 | 3/2011 | Frojd | |
| 2011/0100526 A1* | 5/2011 | Umebayashi | 156/66 |
| 2011/0114520 A1 | 5/2011 | Matthison-Hansen | |
| 2011/0118670 A1 | 5/2011 | Kay et al. | |
| 2011/0137296 A1 | 6/2011 | Tanghoj | |
| 2011/0152843 A1 | 6/2011 | Wedlin et al. | |
| 2011/0178507 A1 | 7/2011 | Bracken et al. | |
| 2011/0184386 A1 | 7/2011 | House | |
| 2011/0213025 A1 | 9/2011 | Finch, Jr. | |
| 2011/0284409 A1 | 11/2011 | Murray et al. | |
| 2012/0029451 A1 | 2/2012 | Conway | |
| 2012/0179144 A1 | 7/2012 | Carleo | |
| 2012/0203182 A1 | 8/2012 | Kay et al. | |
| 2012/0228165 A1 | 9/2012 | Murray et al. | |
| 2012/0271101 A1 | 10/2012 | Tan | |
| 2012/0316515 A1 | 12/2012 | Terry | |
| 2013/0006226 A1 | 1/2013 | Hong et al. | |
| 2013/0037306 A1 | 2/2013 | Kim | |
| 2013/0131647 A1 | 5/2013 | Nielsen | |
| 2013/0138083 A1 | 5/2013 | Tennican | |
| 2013/0138088 A1 | 5/2013 | Nielsen | |
| 2013/0153446 A1 | 6/2013 | Utas et al. | |
| 2014/0142554 A1 | 5/2014 | Conway et al. | |
| 2015/0025489 A1 | 1/2015 | Conway et al. | |

FOREIGN PATENT DOCUMENTS

| | | |
|---|---|---|
| DE | 1913976 U | 4/1965 |
| DE | 19826746 C1 | 11/1999 |
| EP | 0055023 A2 | 6/1982 |
| EP | 0182409 A1 | 5/1986 |
| EP | 0184629 A2 | 6/1986 |
| EP | 0187846 A1 | 7/1986 |
| EP | 0193406 A2 | 9/1986 |
| EP | 0217771 | 4/1987 |
| EP | 0218203 A1 | 4/1987 |
| EP | 0236458 A1 | 9/1987 |
| EP | 0252918 A1 | 1/1988 |
| EP | 0298634 A1 | 1/1989 |
| EP | 0303487 A2 | 2/1989 |
| EP | 0335564 A1 | 10/1989 |
| EP | 0352043 A1 | 1/1990 |
| EP | 0390720 A1 | 10/1990 |
| EP | 0407218 A1 | 1/1991 |
| EP | 0471553 A1 | 2/1992 |
| EP | 0479935 A1 | 4/1992 |
| EP | 0528965 A1 | 3/1993 |
| EP | 0553960 A1 | 8/1993 |
| EP | 0590104 A1 | 4/1994 |
| EP | 0598191 A1 | 5/1994 |
| EP | 0663196 A1 | 7/1995 |
| EP | 0677299 | 10/1995 |
| EP | 0680895 A1 | 11/1995 |
| EP | 0685179 A1 | 12/1995 |
| EP | 0699086 A1 | 3/1996 |
| EP | 0767639 A1 | 4/1997 |
| EP | 0768069 A1 | 4/1997 |
| EP | 0815037 A1 | 1/1998 |
| EP | 0909249 A1 | 4/1999 |
| EP | 0923398 | 6/1999 |
| EP | 0935478 A1 | 8/1999 |
| EP | 0959930 | 12/1999 |
| EP | 0977610 A2 | 2/2000 |
| EP | 1023882 | 8/2000 |
| EP | 1047360 A1 | 11/2000 |
| EP | 1090656 | 4/2001 |
| EP | 1115450 A1 | 7/2001 |
| EP | 1131022 A1 | 9/2001 |
| EP | 1145729 | 10/2001 |
| EP | 1245205 | 10/2002 |
| EP | 1308146 | 5/2003 |
| EP | 1347723 A1 | 10/2003 |
| EP | 1406690 A2 | 4/2004 |
| EP | 1427467 A2 | 6/2004 |
| EP | 1485158 A2 | 12/2004 |
| EP | 1498151 | 1/2005 |
| EP | 1578308 A1 | 9/2005 |
| EP | 1606196 A2 | 12/2005 |
| EP | 1615690 A1 | 1/2006 |
| EP | 1629799 A1 | 3/2006 |
| EP | 1641510 A1 | 4/2006 |
| EP | 1642610 | 4/2006 |
| EP | 1642611 | 4/2006 |
| EP | 1647298 A2 | 4/2006 |
| EP | 1786501 A2 | 5/2007 |
| EP | 1788990 A1 | 5/2007 |
| EP | 1793938 A1 | 6/2007 |
| EP | 1799163 A1 | 6/2007 |
| EP | 1904003 A2 | 4/2008 |
| EP | 1948279 A1 | 7/2008 |
| EP | 1955683 A1 | 8/2008 |
| EP | 2072075 A1 | 6/2009 |
| EP | 2216064 A1 | 8/2010 |
| EP | 2226041 A2 | 9/2010 |
| EP | 2226042 A2 | 9/2010 |
| EP | 2258435 A1 | 12/2010 |
| EP | 2275058 A1 | 1/2011 |
| EP | 2292293 A1 | 3/2011 |
| EP | 2292294 A1 | 3/2011 |
| EP | 2423125 A1 | 2/2012 |
| EP | 2423126 A1 | 2/2012 |
| EP | 2423127 A1 | 2/2012 |
| EP | 2450076 A1 | 5/2012 |
| EP | 2468347 A1 | 6/2012 |
| FR | 1558162 A | 2/1969 |
| FR | 2794638 A1 | 12/2000 |
| FR | 2855399 A1 | 12/2004 |
| GB | 322426 A | 12/1929 |
| GB | 1131865 A | 10/1968 |
| GB | 2150938 A | 7/1985 |
| GB | 2187670 A | 9/1987 |
| JP | 2010-533562 A | 10/2010 |
| JP | 2011-506009 A | 3/2011 |
| WO | 8401102 A1 | 3/1984 |
| WO | 8600816 A1 | 2/1986 |
| WO | 8606284 | 11/1986 |
| WO | 8701582 A1 | 3/1987 |
| WO | 8909626 A1 | 10/1989 |
| WO | 9004431 A1 | 5/1990 |
| WO | 9110466 A1 | 7/1991 |
| WO | 9110467 A1 | 7/1991 |
| WO | 9117728 A1 | 11/1991 |
| WO | 9208426 A1 | 5/1992 |
| WO | 9210220 A1 | 6/1992 |
| WO | 9211826 A1 | 7/1992 |
| WO | 9219192 A1 | 11/1992 |
| WO | 9300054 A1 | 1/1993 |
| WO | 93/11821 A1 | 6/1993 |
| WO | 9311821 A1 | 6/1993 |
| WO | 9314806 A1 | 8/1993 |
| WO | 9406377 A1 | 3/1994 |
| WO | 9416747 A1 | 8/1994 |
| WO | 9426215 A1 | 11/1994 |
| WO | 9508968 A1 | 4/1995 |
| WO | 9509667 A1 | 4/1995 |
| WO | 9517862 A1 | 7/1995 |
| WO | 9534253 A1 | 12/1995 |
| WO | 9600541 A1 | 1/1996 |
| WO | 9604119 A1 | 2/1996 |
| WO | 9619254 A1 | 6/1996 |
| WO | 9626688 A1 | 9/1996 |
| WO | 9630277 A1 | 10/1996 |
| WO | 9634587 A1 | 11/1996 |
| WO | 9638192 A1 | 12/1996 |
| WO | 9639096 A1 | 12/1996 |
| WO | 9725947 A1 | 7/1997 |
| WO | 9726937 | 7/1997 |
| WO | 9741811 | 11/1997 |
| WO | 9806642 A1 | 2/1998 |
| WO | 9907313 A1 | 2/1999 |
| WO | 9930761 A1 | 6/1999 |

(56) References Cited

FOREIGN PATENT DOCUMENTS

| | | |
|---|---|---|
| WO | 9936009 A1 | 7/1999 |
| WO | 0025848 A2 | 5/2000 |
| WO | 0030575 A1 | 6/2000 |
| WO | 0047494 | 8/2000 |
| WO | 0143807 | 6/2001 |
| WO | 0152763 | 7/2001 |
| WO | 0193935 | 12/2001 |
| WO | 0236192 | 5/2002 |
| WO | 02053070 A1 | 7/2002 |
| WO | 02060361 A2 | 8/2002 |
| WO | 03/008028 A2 | 1/2003 |
| WO | 03002178 | 1/2003 |
| WO | 03008029 A2 | 1/2003 |
| WO | 03022333 A1 | 3/2003 |
| WO | 03064279 A1 | 8/2003 |
| WO | 03092779 | 11/2003 |
| WO | 2004004611 A1 | 1/2004 |
| WO | 2004004796 A1 | 1/2004 |
| WO | 2004030722 | 4/2004 |
| WO | 2004032992 A2 | 4/2004 |
| WO | 2004045696 | 6/2004 |
| WO | 2004050155 | 6/2004 |
| WO | 2004052440 | 6/2004 |
| WO | 2004056290 A1 | 7/2004 |
| WO | 2004056414 | 7/2004 |
| WO | 2004056909 A1 | 7/2004 |
| WO | 2004075944 | 9/2004 |
| WO | 2004089454 | 10/2004 |
| WO | 2005004964 | 1/2005 |
| WO | 2005014055 A2 | 2/2005 |
| WO | 2005061035 | 7/2005 |
| WO | 2005092418 | 10/2005 |
| WO | 2006005349 A2 | 1/2006 |
| WO | 2006009509 A1 | 1/2006 |
| WO | 2006009596 A1 | 1/2006 |
| WO | 2006017439 A2 | 2/2006 |
| WO | 2006021590 A1 | 3/2006 |
| WO | 2006027349 A1 | 3/2006 |
| WO | 2006/086250 A2 | 8/2006 |
| WO | 2006097109 A2 | 9/2006 |
| WO | 2006110695 A2 | 10/2006 |
| WO | 2006112782 A1 | 10/2006 |
| WO | 2006130776 A2 | 12/2006 |
| WO | 2007001526 A2 | 1/2007 |
| WO | 2007038988 A1 | 4/2007 |
| WO | 2007083033 A2 | 7/2007 |
| WO | 2008089770 A1 | 7/2008 |
| WO | 2008104603 A1 | 9/2008 |
| WO | 2008138351 A1 | 11/2008 |
| WO | 2008138352 A1 | 11/2008 |
| WO | 2009000277 A1 | 12/2008 |
| WO | 2009012336 A1 | 1/2009 |
| WO | 2009043872 A1 | 4/2009 |
| WO | 2009068043 A2 | 6/2009 |
| WO | 2009080265 A1 | 7/2009 |
| WO | 2009108243 A1 | 9/2009 |
| WO | 2010006620 A1 | 1/2010 |
| WO | 2010054659 A1 | 5/2010 |
| WO | 2010054666 A1 | 5/2010 |
| WO | 2010129362 A1 | 11/2010 |
| WO | 2010130261 A1 | 11/2010 |
| WO | 2010149174 A1 | 12/2010 |
| WO | 2010149175 A1 | 12/2010 |
| WO | 2010151682 A2 | 12/2010 |
| WO | 2011011023 A1 | 1/2011 |
| WO | 2011014201 A1 | 2/2011 |
| WO | 2011019359 A1 | 2/2011 |
| WO | 2011026929 A1 | 3/2011 |
| WO | 2011026930 A1 | 3/2011 |
| WO | 2011063816 A1 | 6/2011 |
| WO | 2011073403 A1 | 6/2011 |
| WO | 2011076211 A1 | 6/2011 |
| WO | 2011079129 A1 | 6/2011 |
| WO | 2011109393 A1 | 9/2011 |
| WO | 2012016570 A2 | 2/2012 |
| WO | 2012016571 A2 | 2/2012 |
| WO | 2012018402 A1 | 2/2012 |
| WO | 2012079590 A1 | 6/2012 |
| WO | 2012134804 A1 | 10/2012 |
| WO | 2013010745 A1 | 1/2013 |
| WO | 2013029621 A1 | 3/2013 |
| WO | 2014081853 A1 | 5/2014 |
| WO | 2014081859 A1 | 5/2014 |

OTHER PUBLICATIONS

Angus Chemie GmbH Technical Data Sheet for AMP-95 dated Mar. 6, 2006.

Ethomeen C/25 Information Sheet dated Jul. 28, 2005.

Johnson, James et al., "Activities of a Nitrofurazone-Containing Urinary Catheter and a Silver Hydrogel Catheter against Multidrug-Resistant Bacteria Characteristic of Catheter-Associated Urinary Tract Infection," Antimicrobial Agents and Chemotherapy, col. 43, No. 12, Dec. 1999, pp. 2990-2995.

Lubrizol Technical Data Sheet, Neutralizing Carbopol®* and Pemulen™ Polymers in Aqueous and Hydroalcoholic Systems, Sep. 16, 2009.

Newman, Diane et al., "Review of Intermittent Catheterization and Current Best Practices," Urol Nurs. 2011:31(1).

PCT/US13/71046 filed Nov. 20, 2013 International Search Report and Written Opinion dated Feb. 21, 2014.

PCT/US13/71060 filed Nov. 20, 2013 International Search Report and Written Opinion dated Jan. 30, 2014.

U.S. Appl. No. 11/104,388, filed Apr. 12, 2005 Notice of Allowance dated Mar. 21, 2014.

U.S. Appl. No. 13/047,175, filed Mar. 14, 2011 Final Office Action dated Mar. 17, 2014.

U.S. Appl. No. 13/682,406, filed Nov. 20, 2012 Non-Final Office Action dated Apr. 21, 2014.

Vapro Product Brochure, 2009.

CN 201380060729.1 filed May 20, 2015 Office Action dated Nov. 4, 2016.

CN 201380060741.2 filed May 20, 2015 Office Action dated Dec. 19, 2016.

EP 12159487.3 filed Mar. 14, 2012 Third Party Observations dated Dec. 2, 2016.

CN 201380060741.2 filed May 20, 2015 First Office Action dated May 3, 2016.

CN201280065776.0 filed Jul. 1, 2014, First Office Action dated Jun. 4, 2015.

CN201280065776.0 filed Jul. 1, 2014, Second Office Action dated Jan. 20, 2016.

PCT/US2012/068248 filed Dec. 6, 2012 International Preliminary Report on Patentability dated Jun. 10, 2014.

EP 12159487.3 filed Mar. 14, 2012 Exam Report dated Jul. 31, 2014.

EP 12159487.3 filed Mar. 14, 2012 Office Action dated Oct. 12, 2015.

EP 12159487.3 filed Mar. 14, 2012 Third Party Observations dated Sep. 8, 2015.

U.S. Appl. No. 13/047,175, filed Mar. 14, 2011 Examiner's Answer dated Nov. 4, 2014.

U.S. Appl. No. 13/682,406, filed Nov. 20, 2012 Final Office Action dated Jun. 5, 2015.

U.S. Appl. No. 13/682,406, filed Nov. 20, 2012 Non-Final Office Action dated Nov. 28, 2014.

U.S. Appl. No. 13/705,695, filed Dec. 5, 2012 Final Office Action dated Apr. 23, 2015.

U.S. Appl. No. 13/705,695, filed Dec. 5, 2012 Non-Final Office Action dated Aug. 26, 2014.

U.S. Appl. No. 14/508,450, filed Oct. 7, 2014 Non-Final Office Action dated Jun. 29, 2015.

EP 13856790.4 filed Apr. 28, 2015 Extended European Search Report dated Jul. 1, 2016.

EP 13857538.6 filed Apr. 29, 2015 Extended European Search Report dated Jun. 17, 2016.

MX/a/2014/005144 filed Apr. 28, 2014 Office Action dated Jul. 14, 2016.

(56) References Cited

OTHER PUBLICATIONS

U.S. Appl. No. 13/682,406, filed Nov. 20, 2012 Examiner's Answer dated Aug. 11, 2016.
CN 201380060741.2 filed May 20, 2015 Office Action dated Aug. 9, 2017.
JP 2015-543141 filed May 19, 2015 Office Action dated Aug. 10, 2017.

* cited by examiner

CATHETER IN BAG WITHOUT ADDITIONAL PACKAGING

FIELD OF THE INVENTION

The present invention relates to a urinary catheter and collection bag that can be provided without additional packaging.

BACKGROUND OF THE INVENTION

Urinary catheter kits include a urinary catheter, a urine collection bag, and, for example, a packet including an antiseptic wipe, a pair of gloves, an absorbent pad, a packet containing water, a lubricant, instructions or product information, or several of these items. Such kits are provided in a package to keep the catheter and other components clean or sterile and to keep them together. For example, the kit can be provided in a bag or tray. The user or health care professional opens the package, removes the several components, and inserts the catheter into the subject. There remains a need for a convenient system to provide clean components and a sterile catheter.

SUMMARY OF THE INVENTION

The present invention relates to a urinary catheter and collection bag that can be provided without additional packaging. The present invention includes a urinary catheter set. This set can include a collection bag and a urinary catheter. The catheter is inside the collection bag. The collection bag is configured as a package for the set. And, the collection bag is the only package for the set.

In an embodiment, the present invention includes a case of urinary catheter sets. The case includes a container and a plurality of the present catheter sets. The plurality of sets in in the container. The collection bag is the only package for the set.

DETAILED DESCRIPTION OF THE INVENTION

Figure 1:
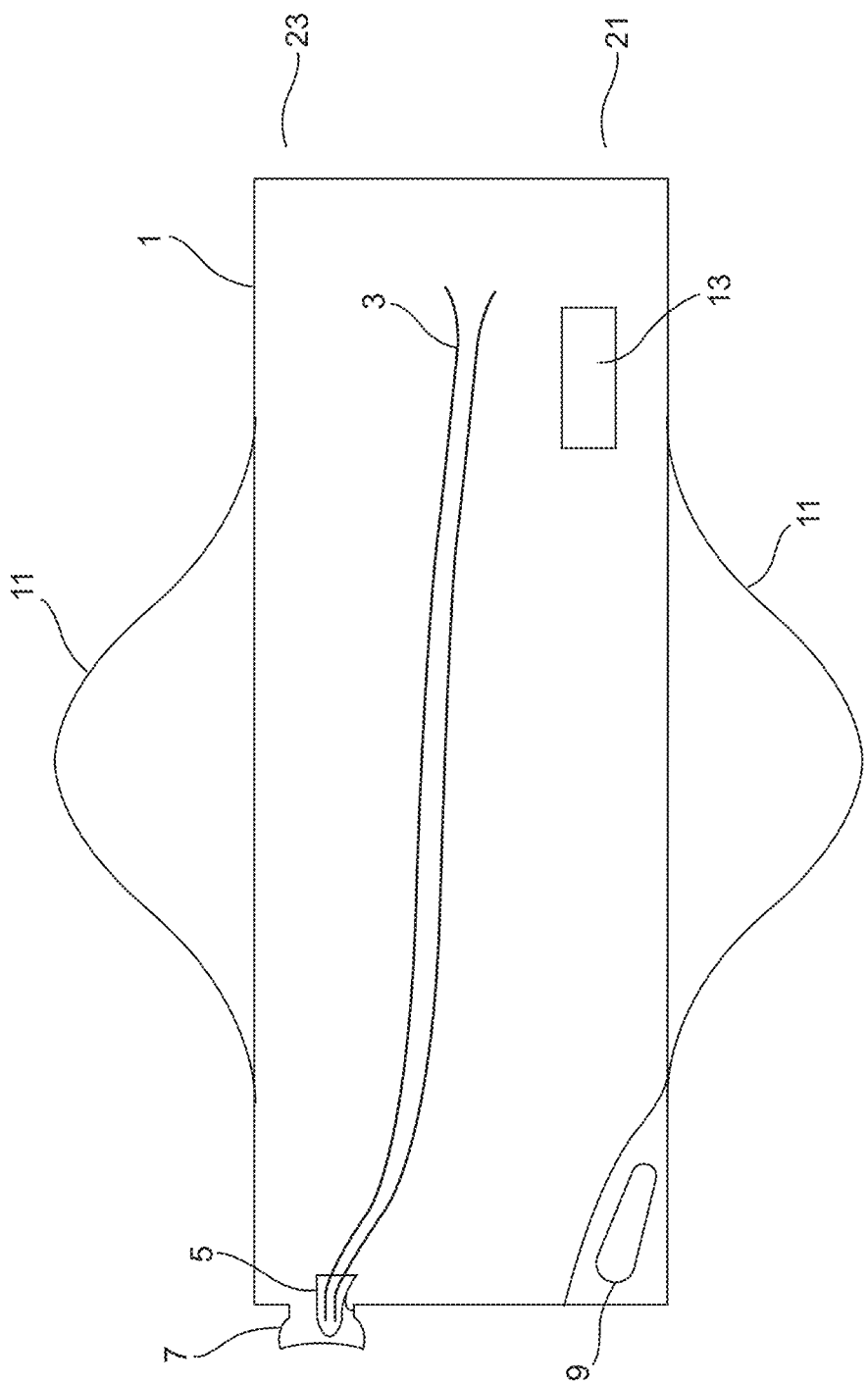
FIG. 1 schematically illustrates an embodiment of the present collection bag and urinary catheter.

The present invention relates to a urinary catheter and collection bag that can be provided without additional packaging. For example, the urinary catheter can be contained in the collection bag and the collection bag can be folded to form a package for the catheter and any additional components or printed information.

In an embodiment, the present invention relates to a catheter set including a collection bag and a urinary catheter. The catheter can be inside the collection bag. The collection bag can be configured as the package for the set. The set is not in packaging beyond the collection bag. The set can also include other items used for or while handling or inserting a urinary catheter. Such items can include an introducer tip, a wipe, a lubricant, a pad, a glove, or a plurality thereof. In the present set, these items are packaged by the collection bag. For example, the collection bag can be folded or wrapped around these items. The collection bag can be coupled to itself when it is folded or wrapped around these items to form (e.g., close or seal) the package.

The present invention includes a urine collection bag configured as a package for the catheter set. As a package, the urine collection bag is folded or wrapped to contain components of the set. The collection bag can be secured around the components it packages. For example, adhesive can couple one portion of the bag to another portion of the bag. For example, a seal (e.g., paper backed with adhesive) can be used to couple one portion of the bag to another portion of the bag. The bag can be secured to itself with sufficient strength to maintain integrity of the package in a case of these packages or when carried by a user or health care professional. The components contained within the folded or wrapped collection bag are not in the interior of the bag. These components may contact the exterior surface of the collection bag, but they do not contact its interior surface.

The interior of the bag is the space in which urine collects when the bag is in use. The catheter and an optional fluid (e.g., water) packet and optional gripping device can be in the interior of the bag. In an embodiment, other components are not in the interior of the bag. After the bag is opened, the end of the catheter that is first introduced into the subject may protrude slightly from the bag when the bag is configured as the package and when the catheter is inside the bag. The end of the catheter that is first introduced into the subject may be inside an introducer tip when the bag is configured as the package. In an embodiment, the entire catheter (including the end that is first introduced into the subject) is inside the bag when the bag is configured as the package with the end that is first introduced into the subject positioned near the opening of the bag. The flow of urine in the catheter enters the bag through the opening of the bag.

The collection bag can include one or more optional flaps to aid in containing the other components of the set. A flap does not include an interior space that can contain urine. Of course, the bag can have a shape that provides regions that define a portion of the interior of the bag but that resemble a flap. As used herein, however, the term flap refers to a portion of the bag that does not define an interior space.

Although the present catheter set does not require or include packaging beyond the bag, individual components of the set may be within their own package. For example, a set including a hydrophilic catheter can include water in a packet. At the time of use of the catheter, the packet is breached to release the water, which increases the slipperiness of the hydrophilic catheter. The packet is a container for the water. The bag as a package contains the water packet. Similarly, a lubricant or a (e.g., antibacterial) wipe can be in a packet. Such a packet is not a package beyond the bag. The bag as package contains the packet of lubricant or wipe. Similarly, a cover for the introducer tip or for the opening in the bag is not packaging beyond the bag.

Components of the set can include, for example, an introducer tip, a wipe, a lubricant, a pad, a glove, or a plurality thereof. Suitable wipes include antibacterial wipes that the person inserting the catheter can use to wipe around the subject's urethra. The wipe can be used on the hands of the person inserting the catheter. The set can include one or more wipes. Each wipe can be in a packet. Suitable pads include an absorbent pad for absorbing any leaked urine. Suitable gloves include plastic or latex gloves, e.g. examination gloves. The gloves can be provided as a pair of gloves. The gloves can be used to prevent contact of the skin of the person inserting the catheter with the catheter and/or tissues near the subject's urethra.

The catheter can be any of a variety of urinary catheters. For example, the catheter can be a hydrophilic catheter. The catheter can be made of silicone rubber and can be latex-free. The entire set can be latex free.

In an embodiment, the present urinary catheter set includes a collection bag and a urinary catheter. The catheter can be inside the collection bag. The collection bag can be configured as a package for the set. And the collection bag is the only package for the set.

The set can also include a fluid packet. The fluid packet can be inside the collection bag. The set can also include an introducer tip, a wipe, a lubricant, a pad, a glove, or a plurality thereof. The introducer tip, wipe, lubricant, pad, glove, or plurality thereof can be packaged by the collection bag. For example, the collection bag can be folded around the introducer tip, wipe, lubricant, pad, glove, or plurality thereof and coupled to itself to form the package for the set. In an embodiment, the set includes the introducer tip, the wipe, the lubricant, the pad, and the glove. In an embodiment, the introducer tip includes an introducer tip cover releaseably coupled to the introducer tip. In an embodiment, the set does not include additional lubricant.

In an embodiment, the present invention includes a case of urinary catheter sets. The case includes a container and a plurality of catheter sets. Each catheter set in the case can include a collection bag and a urinary catheter. The catheter is inside the collection bag, the collection bag is configured as a package for the set, and the set includes no additional packaging. The container contains the plurality of catheter sets. The container can be, for example, a box, a tray, or a bag.

In an embodiment, the urinary catheter can be contained in the collection bag and the collection bag can be folded to form a package for the catheter and any additional components or printed information.

Illustrated Embodiments

FIG. 1 schematically illustrates an embodiment of the present collection bag and urinary catheter. Bag 1 is shown containing straight catheter 3. Straight catheter 3 is equipped with introducer tip 5 proximal opening 7 of bag 1. Bag 1 includes optional grip 9 (an embodiment of the handle) and optional extensions 11 (which are embodiments of the flap). Also shown is sachet 13, which is an embodiment of the fluid packet.

Figure 2:
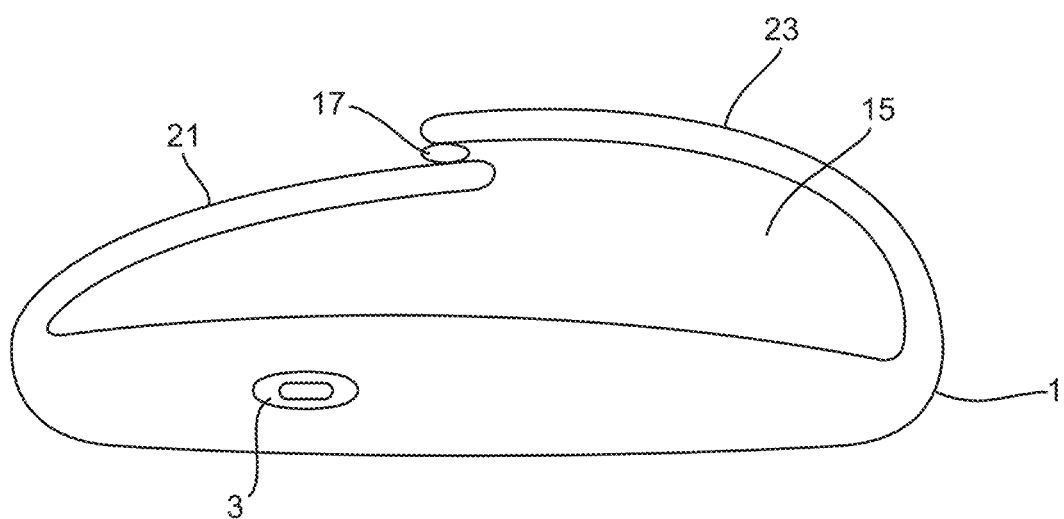
FIG. 2 schematically illustrates a cross sectional view of an embodiment of a bag according to the present invention in a configuration in which it has been wrapped or folded to form a cavity.
Figure 3:
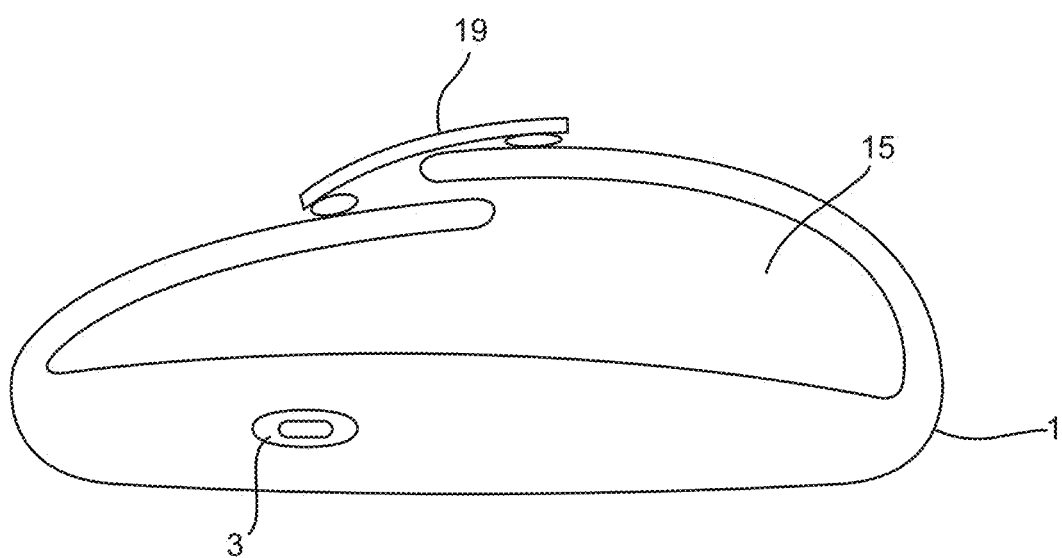
FIG. 3 schematically illustrates a cross sectional view of another embodiment of a bag according to the present invention in a configuration in which it has been wrapped or folded to form a cavity.
Figure 4:
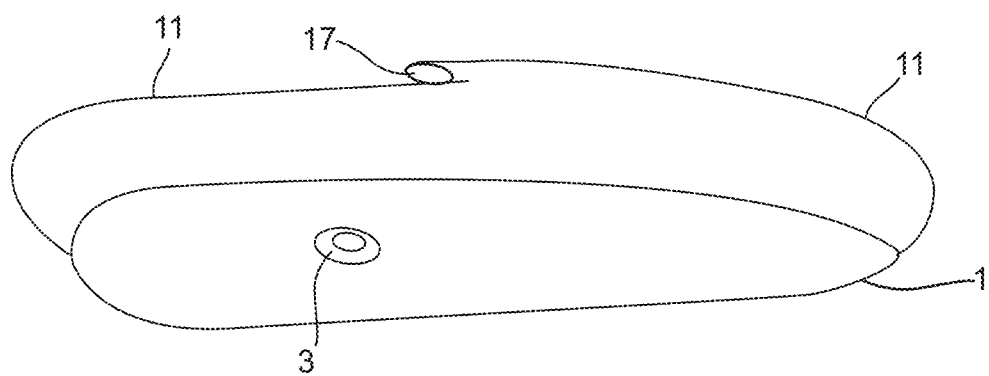
FIG. 4 schematically illustrates a cross sectional view of an embodiment of a bag with extensions according to the present invention in a configuration in which it has been wrapped or folded to form a cavity.

FIG. 2 schematically illustrates a cross sectional view of an embodiment of bag 1 in a configuration in which it has been wrapped or folded to form cavity 15. Cavity 15 can contain additional items such as an introducer tip, a wipe, a lubricant, a pad, a glove, or a plurality thereof. These additional items are not shown in the figures. Bag 1 can be secured in the configuration having cavity 15 by, for example, adhesive 17 or paper seal 19 (FIG. 3). In the embodiment shown in FIGS. 2 and 3, side portions 21 and 23 of bag 1 are folded or wrapped to form cavity 19. FIG. 4 schematically illustrates an embodiment in which two extensions 11 are wrapped or folded to form cavity 19.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A urinary catheter set, comprising:
   a collection bag; and
   a urinary catheter positioned inside of the collection bag, wherein:
   the collection bag is configured as a package for the urinary catheter set,
   the collection bag is the only package for the urinary catheter set,
   the collection bag has a length from an opening in one end of the collection bag to an opposite end of the collection bag, and
   the urinary catheter spans a majority of the length of the collection bag.

2. The urinary catheter set of claim 1, further comprising a fluid packet, the fluid packet positioned inside of the collection bag.

3. The urinary catheter set of claim 1, further comprising one or more elements packaged by the collection bag selected from the group consisting of an introducer tip, a wipe, a lubricant, a pad, and a glove thereof.

4. The urinary catheter set of claim 3, wherein the collection bag is folded around the one or more elements and coupled to itself to form the package for the urinary catheter set.

5. The urinary catheter set of claim 3, wherein:
   the collection bag includes an interior that is configured to collect urine,
   the urinary catheter is inside of the interior of the collection bag, and
   the one or more elements are packaged outside of the interior of the collection bag.

6. The urinary catheter set of claim 1, further comprising an introducer tip, a wipe, a lubricant, a pad, and a glove.

7. The urinary catheter set of claim 1, further comprising an introducer tip, the introducer tip comprising an introducer tip cover releaseably coupled to the introducer tip.

8. The urinary catheter set of claim 1, wherein at least a portion of the urinary catheter is inside of the collection bag in a region where the collection bag is widest.

9. The urinary catheter set of claim 1, wherein the collection bag includes flaps designed to aid in containing one or more elements of the urinary catheter set external to an interior of the collection bag.

10. A case of urinary catheter sets, comprising:
a plurality of urinary catheter sets, each urinary catheter set comprising:
a collection bag and a urinary catheter;
the urinary catheter positioned inside of the collection bag, wherein:
the collection bag is configured as a package for the urinary catheter set,
the urinary catheter set comprises no additional packaging,
the collection bag has a length from an opening in one end of the collection bag to an opposite end of the collection bag, and
the urinary catheter spans a majority of the length of the collection bag; and
a container containing the plurality of urinary catheter sets.

11. The case of urinary catheter sets of claim 10, wherein the container is a box, a tray, or a bag.

12. The case of urinary catheter sets of claim 10, wherein each urinary catheter set further comprises a fluid packet positioned inside of the collection bag.

13. The case of urinary catheter sets of claim 10, wherein each urinary catheter set further comprises an introducer tip, a wipe, a pad, or a glove packaged by the collection bag.

14. The case of urinary catheter sets of claim 13, wherein, in each urinary catheter set, the collection bag includes an interior that is configured to collect urine, wherein the urinary catheter is inside of the interior of the collection bag, and wherein the introducer tip, the wipe, the pad, or the glove is packaged outside of the interior of the collection bag.

15. The case of urinary catheter sets of claim 13, wherein, in each urinary catheter set, the collection bag is folded around the introducer tip, the wipe, the pad, or the glove, and the collection bag is coupled to itself to form the package for the urinary catheter set.

16. The case of urinary catheter sets of claim 10, wherein each urinary catheter set further comprises an introducer tip, a wipe, a lubricant, a pad, and a glove.

17. The case of urinary catheter sets of claim 10, wherein each urinary catheter set further comprises an introducer tip, the introducer tip comprising an introducer tip cover releaseably coupled to the introducer tip.

18. The case of urinary catheter sets of claim 10, wherein, in each urinary catheter set, at least a portion of the urinary catheter is inside of the collection bag in a region where the collection bag is widest.

19. A urinary catheter set, comprising:
a collection bag; and
a urinary catheter positioned inside of the collection bag, wherein:
the collection bag is configured as a package for the urinary catheter set,
the collection bag is the only package for the urinary catheter set, and
at least a portion of the urinary catheter is inside of the collection bag in a region where the collection bag is widest.

20. The urinary catheter set of claim 19, further comprising a fluid packet, the fluid packet positioned inside of the collection bag.

21. The urinary catheter set of claim 19, further comprising one or more elements packaged by the collection bag selected from the group consisting of an introducer tip, a wipe, a lubricant, a pad, and a glove.

22. The urinary catheter set of claim 21, wherein the collection bag is folded around the one or more elements and coupled to itself to form the package for the urinary catheter set.

23. The urinary catheter set of claim 21, wherein:
the collection bag includes an interior that is configured to collect urine,
the urinary catheter is inside of the interior of the collection bag, and
the one or more elements are packaged outside of the interior of the collection bag.

24. The urinary catheter set of claim 19, further comprising an introducer tip, a wipe, a lubricant, a pad, and a glove.

25. The urinary catheter set of claim 19, further comprising an introducer tip, the introducer tip comprising an introducer tip cover releaseably coupled to the introducer tip.

26. The urinary catheter set of claim 19, wherein the collection bag has a length from an opening in one end of the collection bag to an opposite end of the collection bag, and wherein the urinary catheter spans a majority of the length of the collection bag.

27. The urinary catheter set of claim 19, wherein the collection bag includes flaps designed to aid in containing one or more elements of the urinary catheter set external to the interior of the collection bag.

28. A case of urinary catheter sets, comprising:
a plurality of urinary catheter sets, each urinary catheter set comprising:
a collection bag; and
a urinary catheter positioned inside of the collection bag, wherein:
the collection bag is configured as a package for the urinary catheter set,
the urinary catheter set comprises no additional packaging, and
at least a portion of the urinary catheter is inside of the collection bag in a region where the collection bag is widest; and
a container containing the plurality of urinary catheter sets.

29. The case of urinary catheter sets of claim 28, wherein each urinary catheter set further comprises a fluid packet positioned inside of the collection bag.

30. The case of urinary catheter sets of claim 28, wherein each urinary catheter set further comprises an introducer tip, a wipe, a pad, or a glove packaged by the collection bag.

31. The case of urinary catheter sets of claim 30, wherein, in each urinary catheter set, the collection bag includes an interior that is configured to collect urine, wherein the urinary catheter is inside of the interior of the collection bag, and wherein the introducer tip, the wipe, the pad, or the glove is packaged outside of the interior of the collection bag.

32. The case of urinary catheter sets of claim 29, wherein, in each urinary catheter set, the collection bag is folded around the introducer tip, the wipe, the pad, or the glove, and the collection bag is coupled to itself to form the package for the urinary catheter set.

33. The case of urinary catheter sets of claim 28, wherein each urinary catheter set further comprises an introducer tip, a wipe, a lubricant, a pad, and a glove.

34. The case of urinary catheter sets of claim 28, wherein each urinary catheter set further comprises an introducer tip, the introducer tip comprising an introducer tip cover releaseably coupled to the introducer tip.

35. The case of urinary catheter sets of claim 28, wherein, in each urinary catheter set, the collection bag has a length from an opening in one end of the collection bag to an opposite end of the collection bag, and wherein the urinary catheter spans a majority of the length of the collection bag.

\* \* \* \* \*